United States Patent [19]

Triplett

[11] Plant 3,989

[45] Dec. 14, 1976

[54] GRAPEVINE

[76] Inventor: Fay E. Triplett, 749 E. Keyes Road, Ceres, Calif. 95307

[21] Appl. No.: 649,419

[22] Filed: Jan. 14, 1976

[51] Int. Cl.[2] ..... A01H 5/03
[52] U.S. Cl. ..... Plt./47
[58] Field of Search ..... Plt./47

*Primary Examiner*—Robert E. Bagwill
*Attorney, Agent, or Firm*—Roger B. Webster

[57] ABSTRACT

A table-wine variety of grapevine which is vigorous, semi-upright, open, hardy, foliated with medium-size, cordate leaves, and very productive on straight, medium length, medium thick canes, of medium-to-large size, medium length, broad, tapering, regular, loose-to-compact clusters having long stems; the clusters —borne two to three per cane—being short conical in form, and the berries of the clusters being ellipsoidal, strongly adherent, medium size, uniform, black with a thick blue-grey bloom, and having translucent, juicy, greenish flesh, the flesh, of good quality for wine production, being soft, tender, sub-acid, and vinous.

1 Drawing Figure

BACKGROUND OF THE VARIETY

In contemplation of the need for improved table-wine varieties of grapevines, I have—in my vineyard located near Ceres, Stanislaus County, Calif.—undertaken experimental breeding of grapevines for such purpose. The present variety resulted from my endeavors in conducting such experimental breeding program.

ORIGIN OF THE VARIETY

The present variety of grapevine was originated by me in my aforesaid vineyard as a first generation cross of Ruby Cabernet × Barbera (both unpatented).

ASEXUAL REPRODUCTION OF THE VARIETY

Subsequent to its origination by me, I asexually reproduced the present variety of grapevine in my vineyard, located as aforesaid, by cuttings as well as top-working, and—in maturity—such reproductions ran true to the original grapevine in all respects.

SUMMARY OF THE VARIETY

The present table-wine variety of grapevine is vigorous, semi-upright, open, hardy, foliated with medium-size, cordate leaves, and very productive on straight, medium length, medium thick canes, of medium-to-large size, medium length, broad, tapering, regular, loose-to-compact clusters having long stems; the clusters—borne two to three per cane—being short conical in form, and the berries of the clusters being ellipsoidal, strongly adherent, medium size, uniform, black with a thick blue-grey bloom, and having translucent, juicy, greenish flesh; the flesh, of good quality for wine production, being soft, tender, sub-acid, and vinous.

Further, the present variety of grapevine is in harvest relatively early (i.e., medium) so that it rarely encounters rainfall. Additionally, as the stems of the clusters are quite long, hand harvesting by pickers is facilitated.

The present variety of grapevine has certain distinctive characteristics, in comparison to the Ruby Cabernet, as follows:

| | Present Variety | Ruby Cabernet |
|---|---|---|
| VINE: | Very productive | Productive |
| TRUNK: | Medium | Large – medium |
| Bark | Adherent | Long and fissured to stringy |
| CANES: | Medium thickness | Thick |
| Internodes | Medium length | Short to medium length |
| Tendrils | Medium to long<br>Occasionally tri-furcated<br>Often functional | Short to medium length<br>Bifurcated<br>Rarely functional |
| LEAVES: | | |
| Inferior Sinus | Medium depth and width<br>Occasionally sinus nearly absent | Deep |
| Superior Sinus | Medium depth and width<br>Frequently toothed | Deep<br>Occasionally toothed |
| FRUIT: | | |
| Average Date Of Ripening Season | September 15 – 30<br>Medium | September 25 – October 10<br>Medium to late |
| CLUSTERS: | Medium to large | Small to medium |
| Average weight | 554 grams | 289 grams |
| Range | 300 – 690 grams | 225 – 305 grams |
| Average length | 18 cm. | 15.5 cm. |
| Average width | 14.5 cm. | 10.5 cm. |
| | Conical<br>Loose to compact<br>Frequently winged or double-clustered | Long conical<br>Loose to well-filled |
| PEDUNCLE: | | |
| | Long – 5 – 9 cm.<br>Partly lignified<br>Not difficult to cut | Short – 1 – 4 cm.<br>Often lignified<br>Difficult to cut |
| BRUSH: | | |
| Color | Deep wine | Deep wine to maroon |
| BERRIES: | | |
| | Strongly adherent<br>Medium size – 2.0 per berry<br>Ellipsoidal<br>Very good quality | Adherent<br>Medium size – 2.73 grams per berry<br>Round to ellipsoidal<br>Good quality |
| SEEDS: | | |
| | Cuneate<br>Rounded<br>Faintly notched | Cuneate<br>Flattened |
| Beak | Medium<br>Slightly curved | Short<br>Curved |
| Color | Brown | Light brown, with yellowish green tinge |
| Raphe | Medium | Obscure |
| Chalaza | Centrally located to below center<br>Elongated<br>Sunken | Centrally located<br>Slightly sunken |

BRIEF DESCRIPTION OF THE DRAWING

The drawing is an illustration, by photographic reproduction in color, of grape clusters, and leaves.

DESCRIPTION OF THE VARIETY

The botanical details of this new and distinct variety of grapevine—with color definitions (except those in common color terms) referenced to Maerz and Paul Dictionary of Color—are as follows:

Vine:
- *Vigor.*—Vigorous.
- *Growth.*—Semi-upright.
- *Density.*—Open.
- *Hardiness.*—Hardy.
- *Productivity.*—Very productive.

Trunk: Medium size. Medium caliber.
- *Bark.*—Adherent. Shreddy.

Canes: Medium length. Medium number. Medium thickness. Tannish brown (14-j-10). Straight.
- *Nodes.*—Angular.
- *Internodes.*—Medium length.
- *Tendrils.*—Intermittent. Medium thickness. Medium to long. Bifurcated. Occasionally trifurcated. Often functional. Smooth.

Flowers: Fertile.
- *Blooming Period.*—Medium—May 15–May 30.
- *Stamens.*—Upright.

Leaves: Medium size. W × L = 254.0 sq. cm. W/L ratio 1.37. Cordate. Medium thickness.
- *Color.*—Upper Surface—Glossy dark green (24-L-8). Lower Surface—Pale green (22-J-7).
- *Texture.*—Medium.
- *Pubescence.*—Very short, fine hairs on veins. Fine, interlacing hairs in interveinal areas.
- *Lobes.*—Number—5. Terminal Lobe—Acuminate—frequently obtuse.
- *Petiolar Sinus.*—Deep. Frequently toothed. Narrow to closed. Often overlapping.
- *Inferior Sinus.*—Medium depth. Medium width. Frequently toothed.
- *Superior Sinus.*—Medium depth. Medium width. Frequently toothed.
- *Margin.*—Dentate.
- *Teeth.*—Medium depth. Medium width.

Fruit:
- *Date of Ripening.*—September 15–30 depending on seasonal conditions.
- *Season.*—Medium.
- *Keeping Quality.*—Good.
- *Shipping Quality.*—Good.
- *Cluster.*—Medium to large size. 2 – 3 per cane. Weight per cluster—300–690 grams. Medium length—average 18 cm. Broad—average—14.5 cm. Tapering. Short conical. Regular. Shouldered—frequently winged or double-clustered. Loose to compact.
- *Peduncle.*—Long—6–9 cm. Medium thickness.
- *Pedicel.*—Medium length. Medium thickness. Warts.
- *Brush.*—Medium length—5 mm. Wine color.
- *Berries.*—Strongly adherent. Medium size—205.5 grams per 100 berries. Uniform. Ellipsoidal.
- *Color.*—Black to deep bluish purple (48-A-12), with thick blue-grey bloom (37-F-4).
- *Skin.*—Thick. Tough. Adheres to pulp.
- *Flesh.*—Greenish. Translucent. Soft. Juicy. Vinous. Quality—very good.
- *Test Averages.*—Sugar Content (Balling)—22.7. Total Acid (Grams per 100 cc.)—1.09. pH—3.34. The berries of the present variety attain a desirable sugar content without lowering the acid or raising the pH excessively; these factors being most favorable in a table-wine variety of grapevine. The wines made from this grape score very highly in the tastings conducted by expert wine tasters.
- *Seeds.*—Separate from pulp with difficulty. Average number—226 per 100 berries. Medium size. Medium length. Medium breadth. Cuneate. Weight—2.74 grams per 100 seeds. Rounded—lower end rounded, faintly, notched. Beaked—medium size, slightly curved. Brown (8-C-12).
- *Raphe.*—Medium.
- *Chalaza.*—Medium to below center. Oval, or ellipsoidal elongated. Distinct. Sunken.
- *Use.*—Table wine.

The grapevine and its fruit herein described may vary in slight detail due to climatic and soil conditions under which the variety may be grown; the present description being of the variety as grown in the Central Valley of California.

I claim:

1. A new and distinct table-wine variety of grapevine, substantially as illustrated and described, which is vigorous, semi-upright, open, hardy, foliated with medium-size, cordate leaves, and very productive on straight, medium length, medium thick canes, of medium-to-large size, medium length, broad, tapering, reguoar, loose-to-compact clusters having long stems; the clusters—borne two to three per cane—being short conical in form, and the berries of the clusters being ellipsoidal, strongly adherent, medium size, uniform, black with a thick blue-grey bloom, and having translucent, juicy, greenish flesh, the flesh, of good quality for wine production, being soft, tender, sub-acid, and vinous; the variety being more productive, with larger clusters, and ripening earlier than the Ruby Cabernet.

* * * * *

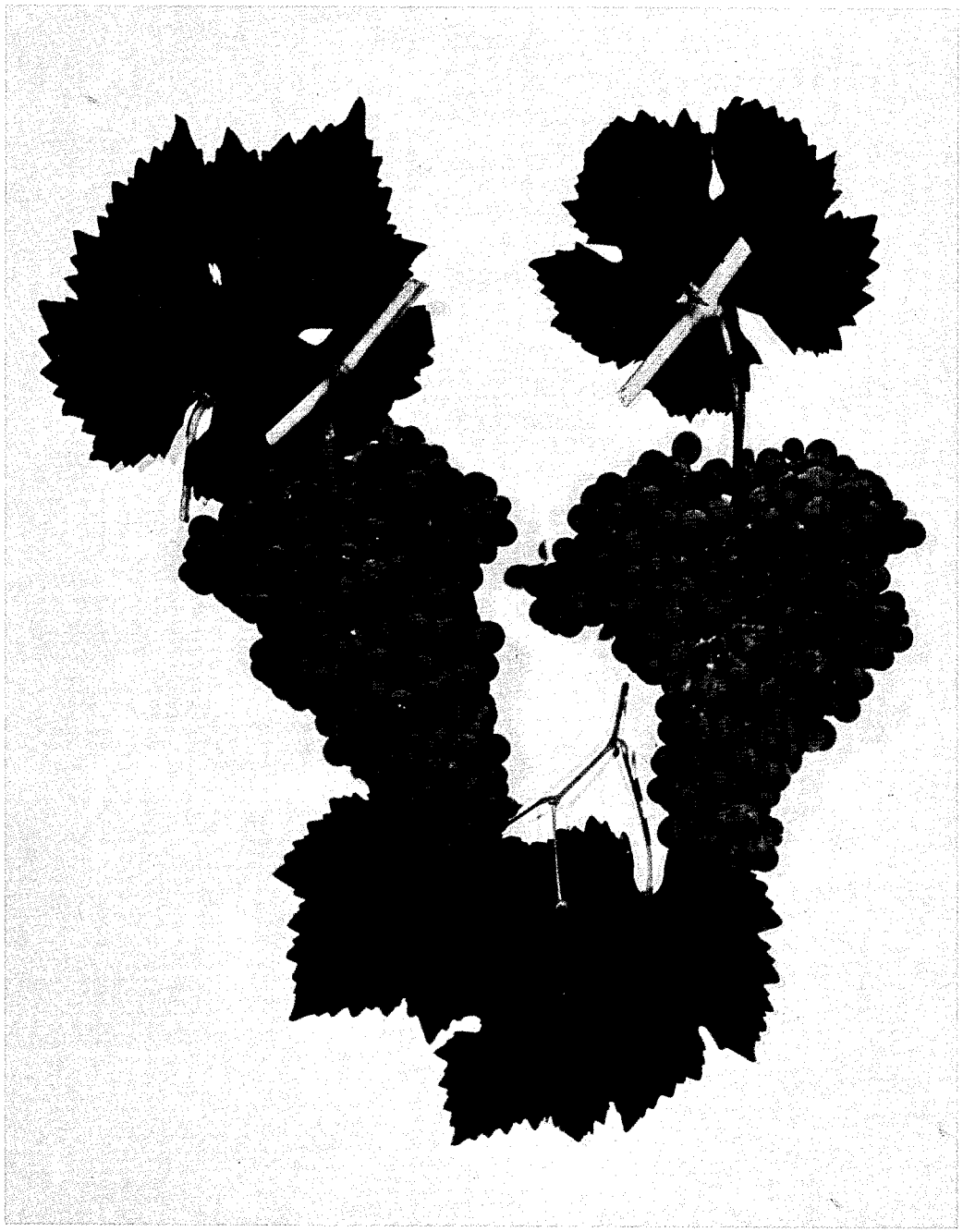

Dec. 14, 1976
F. E. TRIPLETT
GRAPEVINE
Filed Jan. 14, 1976
Plant Pat. 3,989